(12) United States Patent
Li et al.

(10) Patent No.: US 7,805,028 B2
(45) Date of Patent: Sep. 28, 2010

(54) OPTICAL SENSOR AND METHOD EMPLOYING HALF-CORE HOLLOW OPTICAL WAVEGUIDE

(75) Inventors: Zhiyong Li, Redwood City, CA (US); Michael Tan, Menlo Park, CA (US); Shih-Yuan Wang, Palo Alto, CA (US); Wei Wu, Palo Alto, CA (US); Jing Tang, Menlo Park, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 40 days.

(21) Appl. No.: 12/253,123

(22) Filed: Oct. 16, 2008

(65) Prior Publication Data

US 2009/0245718 A1    Oct. 1, 2009

Related U.S. Application Data

(60) Provisional application No. 61/039,399, filed on Mar. 25, 2008.

(51) Int. Cl.
*G02B 6/00* (2006.01)
*G02B 6/32* (2006.01)
*G02B 6/10* (2006.01)

(52) U.S. Cl. .................. 385/12; 385/125; 385/129; 385/146; 356/928; 356/952

(58) Field of Classification Search .......... 356/928–954
See application file for complete search history.

(56) References Cited

U.S. PATENT DOCUMENTS

| | | | |
|---|---|---|---|
| 6,496,634 B1 | 12/2002 | Levenson | |
| 6,845,203 B1 | 1/2005 | Levenson | |
| 7,054,513 B2 | 5/2006 | Herz et al. | |
| 7,136,160 B2* | 11/2006 | Wang | 356/301 |
| 7,142,758 B1 | 11/2006 | Herz et al. | |
| 7,149,396 B2* | 12/2006 | Schmidt et al. | 385/131 |
| 7,283,712 B2 | 10/2007 | Shaw et al. | |
| 2007/0020144 A1 | 1/2007 | Du et al. | |
| 2008/0013877 A1* | 1/2008 | Schmidt et al. | 385/12 |

OTHER PUBLICATIONS

Adrian Amezcua-Correa et al., "Surface-Enhanced Raman Scattering Using Microstructured Optical Fiber Substrates," Adv. Funct. Mater., 2007, 17, pp. 2024-2030.

Felicity M.Cox et al., "Surface enhanced Raman scattering in a hollow core microstructured optical fiber," Optics Express, vol. 15, No. 21, Oct. 2007, pp. 13675-13681.

(Continued)

*Primary Examiner*—Omar Rojas

(57) ABSTRACT

An optical sensor, sensing system and method of sensing employ a half-core hollow optical waveguide adjacent to a surface of an optical waveguide layer of a substrate. The half-core hollow optical waveguide and the adjacent optical waveguide layer cooperatively provide both an optical path that confines and guides an optical signal and an internal hollow channel. The optical path and channel extend longitudinally along a hollow core of the half-core hollow optical waveguide. The system further includes an optical source at an input of the optical path and an optical detector at an output of the optical path. A spectroscopic interaction between an analyte material that is introduced into the channel and an optical signal propagating along the optical path determines a characteristic of the analyte material.

23 Claims, 5 Drawing Sheets

OTHER PUBLICATIONS

T. Ritari et al., "Gas sensing using air-guiding photonic bandgap fibers," Optics Express, vol. 12, No. 17, Aug. 2004, pp. 4080-4087.

Vladimir P. Minkovich et al., "Microstructured optical fiber coated with thin films for gas and chemical sensing," Optics Express, vol. 14, No. 18, Sep. 2006, pp. 8413-8418.

Stephen Smolka et al., "Highly efficient fluorescence sensing with hollow core photonic crystal fibers," Optics Express, vol. 15, No. 20, Oct. 2007, pp. 12783-12791.

Jixin Yang et al., "Surface enhanced Raman scattering using metal modified microstructured optical fiber substrates," Photonic Crystals and Photonic Crystal Fibers for Sensing Applications II, Ed. Henry H. Du, Proc. SPIE, vol. 6369, 636906, 2006, 636906-1-636906-8.

Yi Zhang et al., "Liquid core photonic crystal fiber sensor based on surface enhanced Raman scattering," Applied Physics Letters, 90, 193504, 2007, pp. 193504-1-193504-3.

* cited by examiner

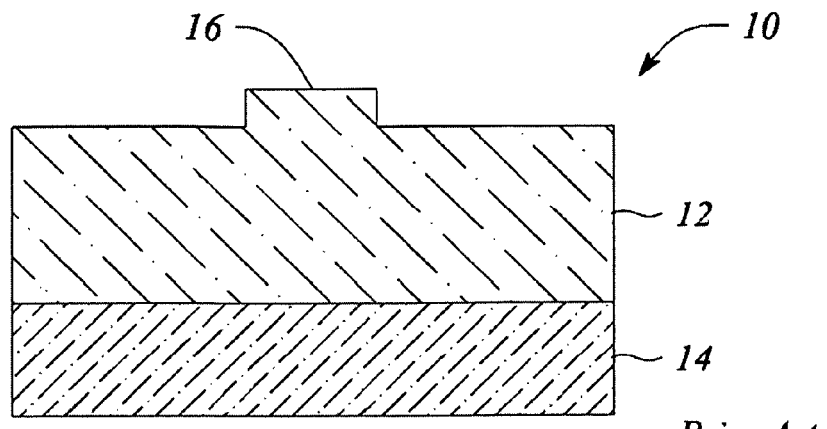
*FIG. 1A*  *Prior Art*
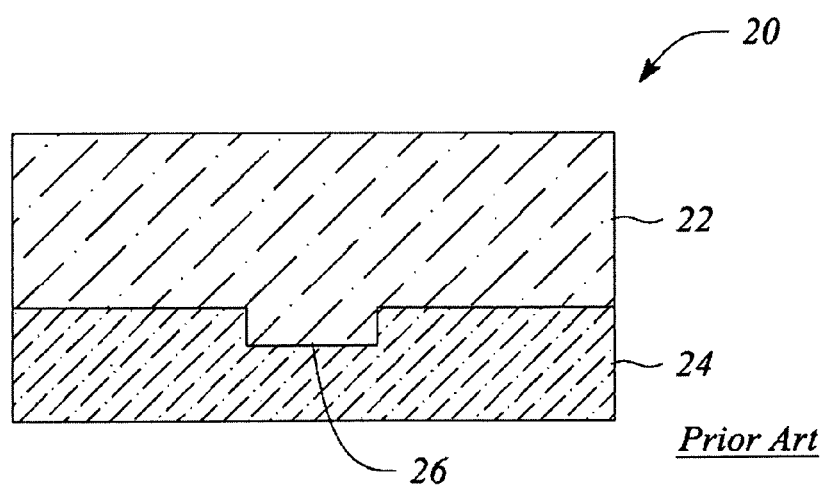
*FIG. 1B*  *Prior Art*
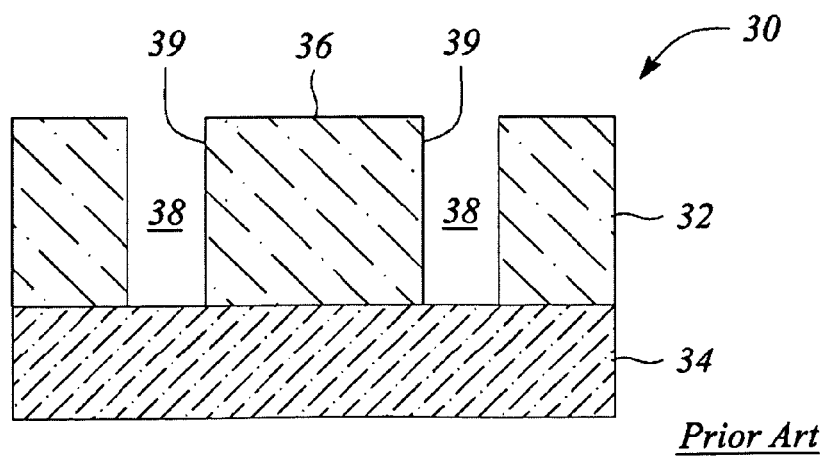
*FIG. 1C*  *Prior Art*

OPTICAL SENSOR AND METHOD EMPLOYING HALF-CORE HOLLOW OPTICAL WAVEGUIDE

CROSS-REFERENCE TO RELATED APPLICATIONS

The present application claims priority from provisional application Ser. No. 61/039,399, filed Mar. 25, 2008, the contents of which are incorporated herein by reference in their entirety.

STATEMENT REGARDING FEDERALLY SPONSORED RESEARCH OR DEVELOPMENT

N/A

BACKGROUND

1. Technical Field

The invention relates to sensors. In particular, the invention relates to sensors that employ optical spectroscopy to analyze a material.

2. Description of Related Art

Spectroscopy is a powerful means for analyzing, characterizing and even identifying a substance or material using one or both of an absorption spectrum and an emission spectrum that results when the material is illuminated by a form of electromagnetic radiation. For example, optical spectroscopy generally involves illuminating the material with an optical signal (e.g., light) and one or both of observing and measuring a spectrum of a response signal produced by an interaction between the optical signal and the material. For example, in optical absorption spectroscopy, an absorption spectrum is compared to a spectrum of the optical signal to determine a spectral 'fingerprint' of the material. In general, the spectral fingerprint is characteristic of the particular material or its constituent parts facilitating identification of the material. Another exemplary form of optical emission spectroscopy is based on Raman-scattering. In Raman-scattering optical spectroscopy, an emission spectrum or spectral components thereof produced by an interaction between the material and the optical signal are associated with particular characteristics (e.g., chemical make-up) of the material. These spectral components contained in a response signal facilitate determination of the material characteristics. An intensity of the Raman-scattering may be significantly enhanced by using a Raman-active material (e.g., Raman-active surface). For example, a Raman-active surface may be employed in surface enhanced Raman-scattering (SERS) optical spectroscopy.

Optical spectroscopy performed in hollow core optical waveguides (e.g., hollow core optical fibers) has generated considerable interest. In particular, using hollow core optical waveguides has the potential of solving some problems and deficiencies that may arise with various forms of optical spectroscopy. For example, the hollow core optical waveguide provides a means for containing the material and one or both of guiding the optical signal to the material and guiding a response signal away from the material. A length over which the material and the optical signal interact (i.e., interaction length) can be made essentially arbitrarily long to increase a signal strength of the response signal, such that detection thereof is improved. Moreover, detection may be further enhanced by using the optical waveguide to preferentially guide the response signal to the detector. However, performing optical spectroscopy in a hollow core optical waveguide presents its own set of problems including, but not limited to, integrating the hollow core optical waveguide with other system components and providing means for introducing enhancement factors (e.g., a Raman-active surface) within the confines of the hollow core optical waveguide.

BRIEF SUMMARY

In some embodiments of the present invention, an optical sensor is provided. The optical sensor comprises an optical waveguide layer adjacent to a surface of a substrate. The optical sensor further comprises a half-core hollow optical waveguide. A half-core side of the hollow optical waveguide is adjacent to a surface of the optical waveguide layer. The half-core hollow optical waveguide and the optical waveguide layer cooperatively form both an optical path that confines and guides an optical signal and an internal hollow channel that extend longitudinally along a hollow core of the half-core hollow optical waveguide. A spectroscopic interaction between an analyte within the channel and an optical signal propagating along the optical path determines a characteristic of the analyte.

In other embodiments of the present invention, an optical sensor system is provided. The optical sensor system comprises an optical waveguide layer in a substrate and adjacent to a surface of the substrate. The optical sensor system further comprises a half-core hollow optical waveguide having a longitudinal axis and a hollow core collinear with the longitudinal axis. The half-core hollow optical waveguide cooperatively forming both an internal hollow channel and an optical path with the optical waveguide layer. The channel is within an optical field region of the optical path. The optical sensor system further comprises an optical source at an input of the optical path and an optical detector at an output of the optical path. The optical detector receives a response signal containing a spectroscopic product of an interaction within the channel between an analyte material to be analyzed and an optical signal produced by the optical source.

In other embodiments of the present invention, a method of optical sensing is provided. The method of optical sensing comprises providing an optical path formed by a half-core hollow optical waveguide adjacent to an optical waveguide layer of a substrate. The half-core hollow optical waveguide has a hollow core that cooperatively forms an internal channel with a surface of the substrate such that the channel extends along the optical path. The method of optical sensing further comprises introducing an analyte into the channel and interacting an optical signal with the analyte within the channel to produce a spectroscopic response. The optical signal and the spectroscopic response are guided along the optical path, wherein the spectroscopic response is characteristic of the material.

Certain embodiments of the present invention have other features that are one or both of in addition to and in lieu of the features described hereinabove. These and other features of the invention are detailed below with reference to the following drawings.

BRIEF DESCRIPTION OF THE DRAWINGS

The various features of embodiments of the present invention may be more readily understood with reference to the following detailed description taken in conjunction with the accompanying drawings, where like reference numerals designate like structural elements, and in which:

FIG. 1A illustrates a cross sectional view of a conventional slab optical waveguide known as a ridge-loaded optical waveguide.

FIG. 1B illustrates a cross sectional view of another conventional slab waveguide known as a reverse ridge-loaded optical waveguide.

FIG. 1C illustrates a cross sectional view of an exemplary conventional strip optical waveguide.

DETAILED DESCRIPTION

Figure 2A:
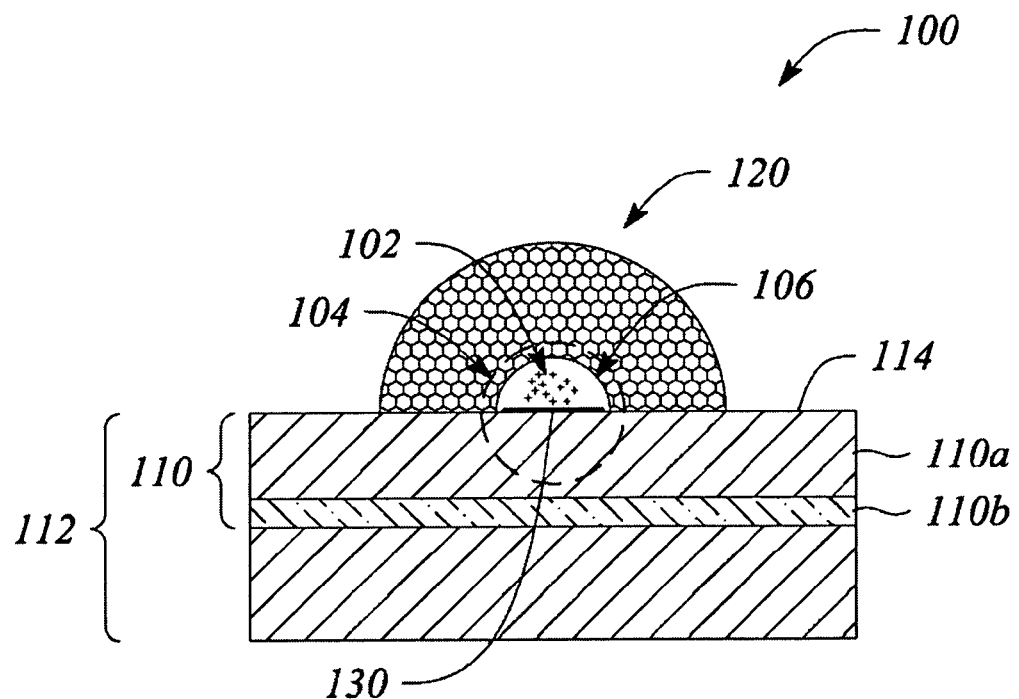
FIG. 2A illustrates a cross sectional view of an optical sensor, according to an embodiment of the present invention.

Embodiments of the present invention employ an optical waveguide with an interior hollow space or channel to facilitate sensing or characterizing a substance or material. In particular, the substance or material is characterized within the channel of the optical waveguide using optical spectroscopy. The material to be analyzed or 'analyte', contained or confined by the channel within an optical field region of the optical waveguide is illuminated by and interacts with an optical signal. The interaction produces a spectral product or response signal that contains information about the analyte that may used to characterize and identify the analyte material. Both the optical signal and the response signal are guided by the optical waveguide. Various embodiments of the present invention include, but are not limited to, an optical sensor, an optical sensing system and a method of sensing. For example, the analyte may be a chemical or biological analyte. The optical spectroscopy may employ one or more of surface enhanced Raman scattering (SERS), surface enhanced resonant Raman scattering (SERRS), surface enhanced hyper Raman scattering (SEHRS), optical absorption, luminescence and fluorescence, for example.

Embodiments of the present invention provide a relatively long interaction length between the analyte and the optical signal. Specifically, long interaction length may be achieved by employing an extended length of optical waveguide. Further, the analyte may be confined by the channel within a high optical field region of the illuminating optical signal along the extended length. In some applications, the relatively long interaction length may improve a strength or intensity of the response signal of the optical spectroscopy. Increased response signal strength may improve one or both of a sensitivity of the optical spectroscopy and an accuracy of the optical spectroscopy, for example.

In addition to confining the analyte within the optical field region of the optical waveguide, the channel may facilitate analyte introduction and removal. For example, the analyte may be either in the form of a fluid or an analyte material carried by a fluid carrier (e.g., as colloidal suspension in a liquid or a particle suspended in a gas). The fluid may be introduced to and removed from the active region by allowing the fluid to flow into and subsequently out of the channel. Since the channel is inside of the optical waveguide, a guiding property of the optical waveguide insures that the optical signal and the analyte are collocated within a region containing an optical field of the optical signal. In some embodiments, the collocation is in a high optical field region.

Moreover as mentioned above, spectral products (i.e., the response signal) generated during the interaction between the analyte in the channel and the optical signal may be guided by the optical waveguide to facilitate detection and analysis of the generated spectral products. For example, when the optical spectroscopy involves surface enhanced Raman scattering (SERS), the interaction produces a SERS response signal, which is subsequently guided by the optical waveguide. A detector located at an output end of the optical waveguide may receive a substantially greater portion of the generated SERS response signal than in a conventional SERS implementation. As such, the guiding of the SERS response signal by the optical waveguide ultimately may provide for a more efficient or enhanced detection than without the guiding.

Embodiments of the present invention facilitate optical spectroscopy that may employ various coatings or related spectroscopy-assist materials within an interaction region of the channel. In particular, various embodiments of the present invention comprise a two-part channel that is assembled. Since the channel is initially in two parts, ready access is provided to an interior of the channel during manufacturing. For example, in an exemplary optical spectroscopy that employs SERS, SERRS or SEHRS, the two-part channel facilitates providing a Raman-active surface within the channel. The Raman-active surface may be deposited and patterned by conventional semiconductor fabrication methodologies before the two-part channel is assembled.

Embodiments of the present invention further facilitate integrating an optical sensor with other components of a sensor system. Other components may include, but are not limited to, an optical source (e.g., a laser) that produces the optical signal and a detector for determining results of the optical spectroscopy, for example. In another example, microfluidic channels and related components may be integrated with the optical sensor to facilitate introduction and removal of the analyte being sensed.

The various other components may be fabricated on or in a substrate that is common to both the other components and the optical sensor, according to some embodiments of the present invention. The other components may be one or both of monolithically fabricated within the common substrate and separately fabricated and wafer bonded on a surface of the common substrate. Among the other components that may be monolithically fabricated within or wafer bonded on a surface of the common substrate are the optical source, the detector and various application specific integrated circuit (ASIC) components used to process the determined results. Similarly, the microfluidic channels and related microfluidic control components may be formed in or on the common substrate. The common substrate may be a substrate that provides a slab waveguide (described below), further facilitating integration of the other components with the optical sensor, for example.

Embodiments of the present invention comprise a half-core hollow optical waveguide. A hollow core of the half-core hollow optical waveguide provides or serves as a first part of the two-part channel. The half-core hollow optical waveguide comprises a hollow optical waveguide that is bisected at the core along and collinear with a longitudinal axis of the hollow optical waveguide. The bisection exposes a hollow core (or a core part of the channel) within the hollow optical waveguide. In general, the bisection effectively divides the hollow optical waveguide approximately in half along the longitudinal axis yielding two longitudinal half-portions. However, while the bisection produces two half-portions with exposed longitudinal half-core sides, the two half-portions may be of unequal hollow core extent so long as the channel within the hollow optical waveguide is at least partially exposed or opened by die bisection. Such a half-portion of the bisected hollow optical waveguide is defined and referred to herein as the 'half-core hollow optical waveguide'.

The hollow optical waveguide may be essentially any optical waveguide structure that has a hollow or partially hollow area or channel within and extending along a guided optical field region (i.e., optical path) of the hollow optical waveguide. In particular, any optical waveguide that confines a portion of the optical field of a propagating optical signal to a region of optical waveguide that includes the channel may be employed. The term 'optical path' is defined as a path to which an optical signal propagating in the optical waveguide is confined and is guided by the optical waveguide.

For example, the hollow optical waveguide may be a metal channel optical waveguide. A metal channel optical waveguide comprises a metal wall that surrounds and encloses a central channel through which an optical signal is guided by multiple reflections from the metal wall. The central channel is generally hollow such that it may be filled with air or a fluid when employed according to some embodiments of the present invention. The optical path of the metal channel optical waveguide is essentially defined by the central channel.

In another example, the hollow optical waveguide may comprise a photonic crystal optical waveguide (i.e., photonic crystal fiber). A photonic crystal optical waveguide employs properties of photonic crystals to confine and guide an optical signal. In particular, a photonic crystal optical waveguide comprises a photonic crystal that surrounds a core region. Characteristics of the surrounding photonic crystal essentially prohibit propagation of light, often at certain frequencies, within the photonic crystal. Since light cannot propagate within the photonic crystal, the light also is effectively prevented from entering or penetrating the photonic crystal. As such, light propagating in the core of the photonic crystal optical waveguide is confined in and guided along the core.

Moreover, since light is confined to the core by the action of the photonic crystal, a refractive index of a material within the core region and a difference between that refractive index and a refractive index of the surrounding photonic crystal is relatively unimportant. Consequently, the core region need not have a higher index of refraction than the surrounding photonic crystal as is normally required in a conventional or 'index-guided' optical waveguide. For example, the core region may be partially or completely hollow (e.g., filled with air or liquid). Photonic crystal optical waveguides are also referred to as microstructured optical waveguides or microstructured fibers (MOFs). Photonic crystal optical waveguides with hollow cores or channels that are suitable for use as the hollow core optical waveguide according to some embodiments of the present invention include, but are not limited to, hollow core photonic bandgap optical fibers, holey optical fibers, various related microstructured fibers with hollow cores, and hollow core Bragg optical fibers.

A photonic bandgap (PBG) optical fiber is a fiber that has a PBG structure or crystal in a material surrounding a core (e.g., the hollow core). The PBG crystal generally comprises a regular array of discontinuities in a dielectric material. For example, the PBG crystal may be an array of holes in the dielectric material. In another example, the discontinuities are formed by an array of objects within the dielectric material, wherein the objects differ from the dielectric material and include, but are not limited to, metal objects and dielectric objects with a different dielectric constant. For example, the objects may be spheriod particles of dielectric material suspended within a dielectric matrix of the PBG crystal. Alternatively, the particles may be cubical or have another complex shape.

A holey fiber is a photonic crystal optical waveguide comprising a plurality of holes extending collinearly with a longitudinal axis of the fiber. The plurality of holes act to confine light to propagate in a core region of the holey fiber. For example, the holes may be randomly arranged to produce an effective dielectric profile in a cross section of the holey fiber that confines the light. The random arrangement of the holes may be such that a density of the holes in the core region is lower than a density of holes in a surrounding, cladding region of the fiber, for example. The density difference of the holes produces a difference in an effective index of refraction between the core region and the cladding region that confines light to and guides light within the core region. Essentially the density difference provides an 'optically confining' effective dielectric profile within a cross section of the fiber. In another example, the holes are regularly arranged to provide the optically confining effective dielectric profile. The density difference may be provided by regularly spaced or ordered array of holes in the core and cladding regions, for example. In yet another example, the holes may be arranged in a regular array around an essentially hollow core region. In this example, the holey fiber may be essentially similar to a hollow core PBG optical fiber.

The Bragg fiber comprises a core surrounded by concentric layers of materials that effectively act as a Bragg mirror. As such, light propagating in the core is confined by reflection from the Bragg mirror that surrounds the core. For example, concentric thin film layers of alternating dielectric materials having respective different dielectric constants may act as the Bragg mirror. Since the light is confined by reflection from the surrounding Bragg mirror, a material of the core is relatively unimportant. As such, the Bragg fiber may have a hollow core and function as the hollow core optical fiber according to the present invention.

Embodiments of the present invention further comprise a substrate. The channel (e.g., two-part channel) that confines the analyte is formed in part by the exposed hollow core (i.e., first part) and in part by the substrate to which the half-core hollow optical waveguide is affixed. In particular, the half-core hollow optical waveguide is affixed to the substrate such that the exposed hollow core is adjacent to the substrate. A surface of the substrate acts as a first wall of the internal hollow channel while an interior wall of the exposed hollow core serves as a second wall of the internal hollow channel. Together the first and second walls surround and define the channel In other words, the substrate or a surface thereof acts as a second part of the two-part channel.

The substrate comprises a layer adjacent to the substrate surface that facilitates propagation of light when mated with the half-core hollow optical waveguide. In particular, when mated, the half-core hollow optical waveguide and substrate layer combine to define and create an optical path. The substrate layer adjacent to the substrate surface is referred to and defined herein as an 'optical waveguide layer'. The optical waveguide layer may be essentially any structure that in conjunction with the half-core hollow optical waveguide facilitates the propagation of the optical signal along the optical path. Specifically, the combination of the optical waveguide layer and the adjacent half-core hollow optical waveguide create and provide the optical path.

In some embodiments, the optical waveguide layer comprises a slab optical waveguide or 'slab waveguide'. A basic slab waveguide comprises an optical transmission layer and a boundary layer. The optical transmission layer is a layer of an essentially optical transmissive (e.g., optically transparent) material adjacent to a surface of the optical waveguide layer. The boundary layer is layer generally located below the optical transmission layer on a side of the optical transmission layer opposite the surface. The boundary layer acts to confine an optical signal in a vertical direction (e.g., z-direction) by essentially preventing the optical signal from penetrating down into the substrate. As such, the optical signal is guided along the surface essentially propagating only within the optical transmission layer.

The boundary layer may comprise essentially any material or combination of materials that inhibits optical signal propagation into and through the boundary layer. For example, the boundary layer may comprise a material having a lower refractive index than an index of refraction of the optical transmission layer. The difference in refractive indices effectively confines the optical signal to the transmission layer. A layer of silicon (Si) adjacent to a surface of a silicon on insulator (SOI) substrate may function as the slab waveguide, for example. In another example, the boundary layer comprises a plurality of alternating layers that act as a Bragg mirror to prevent propagation of the optical signal in a vertical or z-direction.

The basic slab waveguide described above guides the optical signal by confining it to the optical transmission layer. A direction of propagation along the surface (e.g., in an x-direction or y-direction) is not controlled in the basic slab waveguide. However, other types of slab waveguides besides the basic slab waveguide do provide lateral guiding of signal propagation as well as vertical signal confinement.

FIG. 1A illustrates a cross sectional view of a conventional slab optical waveguide known as a ridge-loaded optical waveguide 10. The ridge-loaded optical waveguide 10 is also sometimes referred to as a 'ridge-loaded waveguide' or simply a 'ridge waveguide'. The ridge-loaded waveguide comprises a transmission layer 12.

The transmission layer 12 comprises a dielectric material through which an optical signal propagates and is guided within the ridge-loaded waveguide 10. In general, the transmission layer 12 comprises a dielectric material or a semiconductor material, which behaves essentially as a dielectric material with respect to its use in an optical waveguide. Moreover, the material of the transmission layer 12 is essentially transparent to the optical signal.

For example, the transmission layer 12 may comprise a semiconductor material that is compatible with the optical signal such as, but not limited to, silicon (Si), gallium arsenide (GaAs), and lithium niobate (LiNbO$_3$). Dielectric materials used for the transmission layer 12 may include, but are not limited to, glass (e.g., borosilicate glass) and various polymers (e.g., polycarbonate). Any of a single crystalline, poly crystalline or amorphous layer of the dielectric material or the semiconductor material may be employed, according to various embodiments. The transparency of the transmission layer 12 material affects an optical loss of the ridge-loaded waveguide. For example, the less transparent the material, the more loss is experienced by the optical signal.

In some embodiments, the transmission layer 12 is supported by a boundary layer 14. The boundary layer 14 physically supports the transmission layer 12. In some embodiments, the boundary layer 14 also facilitates optical confinement in the transmission layer 12. In some embodiments, the boundary layer 14 may comprise a material that differs from the material of the transmission layer 12. In particular, the boundary layer 14 may comprise a material having a refractive index that is different from a refractive index of the transmission layer 12. For example, the boundary layer 14 may be an oxide-based insulator layer (e.g., silicon oxide). In another example, the boundary layer 14 is an insulator layer of an SOI substrate. In some embodiments, the different refractive index of the boundary layer 14 serves to essentially confine the optical signal to the transmission layer 12. In some embodiments, the transmission layer 12 may comprise a thin film layer deposited on an underlying layer or an underlying supporting substrate (not illustrated). In such embodiments, the ridge-loaded waveguide 10 may be termed a 'thin film' ridge-loaded waveguide 10.

The ridge-loaded waveguide 10 further comprises a ridge 16. The ridge 16 is located on and extends above a top surface of the transmission layer 12. The ridge 16 serves to 'guide' the optical signal within the transmission layer 12. In particular, essentially all of the optical energy of the optical signal is concentrated adjacent to the ridge 16 within the transmission layer 12.

The ridge 16 may be formed by one or more of an etching process, a selective deposition process, or a printing process, for example. A particular width and height of the ridge 16 are generally a function of a refractive index of the transmission layer 12 material. Information for determining the width and the height may be readily-obtained from conventional design guidelines and using computer design models for ridge-loaded optical waveguides.

FIG. 1B illustrates a cross sectional view of another conventional slab waveguide known as a reverse ridge-loaded optical waveguide 20. The reverse ridge-loaded optical waveguide 20 is also referred to simply as a 'reverse ridge-loaded waveguide' or a 'reverse ridge waveguide' herein.

The reverse ridge-loaded waveguide 20 comprises a transmission layer 22. The reverse ridge-loaded waveguide 20 further comprises a boundary layer 24. The boundary layer 24 comprises a material having a refractive index that differs from a refractive index of the transmission layer 22. The transmission layer 22 is essentially similar to the transmission layer 12 of the ridge-loaded waveguide 10 described above, according to some embodiments. Further, the boundary layer 24 may be essentially similar to the boundary layer 14 of the ridge-loaded waveguide 10 described above, according to some embodiments. In some embodiments, the transmission layer 22 comprises a thin film layer deposited on the boundary layer 24, wherein the boundary layer 24 is lying on a supporting substrate (not illustrated). In such embodiments, the reverse ridge-loaded waveguide 20 may be termed a 'thin film' reverse ridge-loaded wave guide 20.

The reverse ridge-loaded waveguide 20 further comprises a ridge 26. The ridge 26 extends from an interface between the boundary layer 24 and the transmission layer 22 down and into the boundary layer 24. As with the ridge 16 of the ridge-loaded waveguide 10 described above, the ridge 26 of the reverse ridge-loaded waveguide 20 serves to guide the optical signal within the transmission layer 22.

In other embodiments, the optical waveguide layer may comprise other optical transmission structures, such as, but not limited to, a strip waveguide and a half-core hollow waveguide, for example. FIG. 1C illustrates a cross sectional view of an exemplary conventional strip optical waveguide 30. The strip optical waveguide 30, or simply 'strip waveguide' 30, comprises a strip layer 32 and a boundary layer 34. The strip optical waveguide 30 further comprises a strip 36 formed in or from the strip layer 32. In particular, the strip 36 may be formed in the strip layer 32 by etching channels 38 to define the strip 36, as illustrated in FIG. 1C. The channels 38 optically isolate the strip 36 from the strip layer 32. In other embodiments, the strip waveguide comprises the strip 36 formed from the strip layer 32, but without channels (not illustrated). For example, the strip layer 32 is removed by etching until only the strip 36 remains during fabrication. As such, channels in the strip layer 32 are not formed.

In contrast to the slab waveguides 10, 20, the optical energy within the strip waveguide 30 is essentially confined to the strip 36 by the presence of sidewalls 39 of the strip 36. A material boundary exists at the sidewalls 39 between a material of the strip layer 32 and air or another dielectric material within the channels 38. The boundary represents a change in a refractive index across the boundary. The refractive index change causes an optical signal to be tightly bound to the strip 36 due to total internal reflection therewithin.

For simplicity herein, no distinction is made between a substrate or slab and any layer or structure on the substrate/slab unless such a distinction is necessary for proper understanding. Also herein, the terms 'analyte', 'analyte material' are used interchangeably to mean a material being one or more of analyzed, characterized and identified according to the present invention. Further, as used herein, the article 'a' is intended to have its ordinary meaning in the patent arts, namely 'one or more'. For example, 'a layer' generally means one or more layers and as such, 'the layer' means 'the layer(s)' herein. Also, any reference herein to 'top', 'bottom', 'upper', 'lower', 'up', 'down', 'left' or 'right' is not intended to be a limitation herein. Moreover, examples herein are intended to be illustrative only and are presented for discussion purposes and not by way of limitation.

Figure 2B:
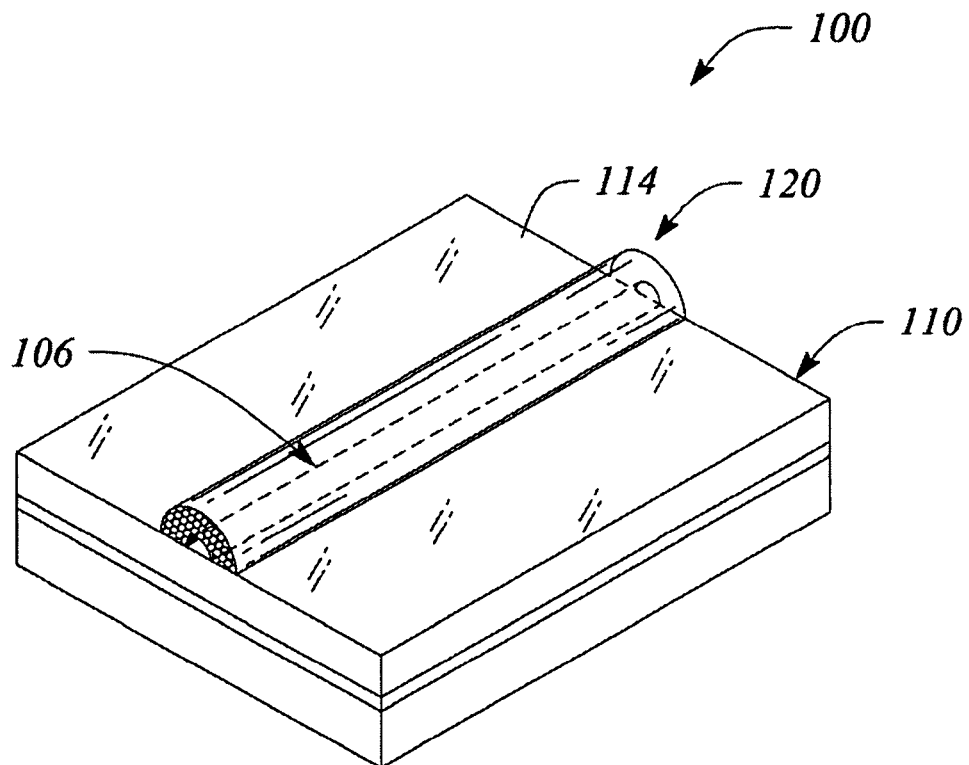
FIG. 2B illustrates a perspective view of the optical sensor illustrated in FIG. 2A, according to an embodiment of the present invention.

FIG. 2A illustrates a cross sectional view of an optical sensor 100, according to an embodiment of the present invention. FIG. 2B illustrates a perspective view of the optical sensor 100 illustrated in FIG. 2A, according to an embodiment of the present invention. The optical sensor 100 determines a characteristic of analyte 102 using optical spectroscopy. In particular, a spectroscopic interaction between the analyte 102 and an optical signal propagating along an optical path 104 determines the characteristic of the analyte 102. The analyte 102 is confined in a channel 106 during optical spectroscopy. For example, the analyte 102 may be a fluid flowing in and through the channel 106. An exemplary dashed closed curve (i.e., circle) in FIG. 2A indicates an approximate extent of a cross sectional area of the optical path 104.

The optical sensor 100 comprises an optical waveguide layer 110. In some embodiments, the optical waveguide layer 110 is a layer of a substrate 112. In particular, the optical waveguide layer 110 is adjacent to a surface 114 of the substrate 112. For example, the optical waveguide layer 110 may be a top layer of the substrate 112, as illustrated. The surface 114 of the substrate 112 and by extension, a surface of the optical waveguide layer 110 act as a wall of the channel 106. A portion of the optical path 104 may extend into the optical waveguide layer 110, in some embodiments, as illustrated by a portion of the dashed closed circle in the optical waveguide layer 110.

In some embodiments, the optical waveguide layer 110 comprises a slab waveguide 110 as illustrated in FIGS. 2A-2B. The slab waveguide 110 comprises a transmission layer 110a and a boundary layer 110b In some embodiments, the optical waveguide layer 110 comprises a ridge-loaded waveguide such as is illustrated in FIG. 1B. The ridge of the ridge-loaded waveguide may be located within the channel 106, for example In some embodiments, the optical waveguide layer 110 comprises a reverse ridge-loaded waveguide such as is illustrated in FIG. 1B. The ridge of the reverse ridge-loaded waveguide may be located directly below and collinear with the channel 106, for example. In yet other embodiments, another optical waveguide structure besides a slab waveguide is employed as the optical waveguide layer 110. For example, the optical waveguide layer 110 may comprise a strip optical waveguide such as is illustrated in FIG. 1C. In an exemplary implementation, the strip may be located directly below and essentially collinear with the channel 106.

In some embodiments, a thickness of a guiding structure of the optical waveguide layer 110 (e.g., slab waveguide, ridge-loaded waveguide, etc.) may be reduced compared to a conventional guiding structure. By reducing the thickness, an optical field (e.g., optical energy of the optical field) of the guided optical signal may be concentrated in a vicinity of the channel 106 as opposed to being essentially located entirely within the guiding structure of the optical waveguide layer 110. In other words, the optical path 104 is preferentially forced upward by the relatively thinner optical waveguide layer 110 such that the optical path 104 envelopes the channel 106 as is illustrated by the location of the dashed closed circle in FIG. 2A.

As illustrated in FIGS. 2A and 2B, the optical sensor 100 further comprises a half-core hollow optical waveguide 120. The half-core hollow optical waveguide 120 is positioned adjacent to the surface 114 of the substrate 112 containing the optical waveguide layer 110. A combination of the optical waveguide layer 110 and the adjacent half-core hollow optical waveguide 120 form both the channel 106 and the optical path 104 that confines and guides the optical signal.

The half-core hollow optical waveguide 120 has a hollow core that extends collinearly along a longitudinal axis of the optical waveguide 120. In particular, the hollow half-core extends along the optical path. An interior surface of the hollow half-core forms another wall of the channel 106. The optical path 104 further confines the optical signal to propagate in a vicinity of the channel 106. For example, the optical path 104 may confine the optical signal in a vicinity of the channel 106 such that a high field region of the optical signal is coincident with the channel 106.

The half-core hollow optical waveguide 120 may be essentially any hollow core optical waveguide that is bisected to expose the hollow core as was discussed above. In particular, the half-core hollow optical waveguide 120 may comprise a portion of a bisected holey optical waveguide, in some embodiments. In such embodiments, the hollow core is a bisected hole of the holey optical waveguide. In other embodiments, the half-core hollow optical waveguide 120 comprises a portion of a bisected hollow metal channel waveguide. In yet other embodiments, bisected ones of various other hollow core optical waveguides are employed as the half-core optical waveguide 120.

Figure 3:
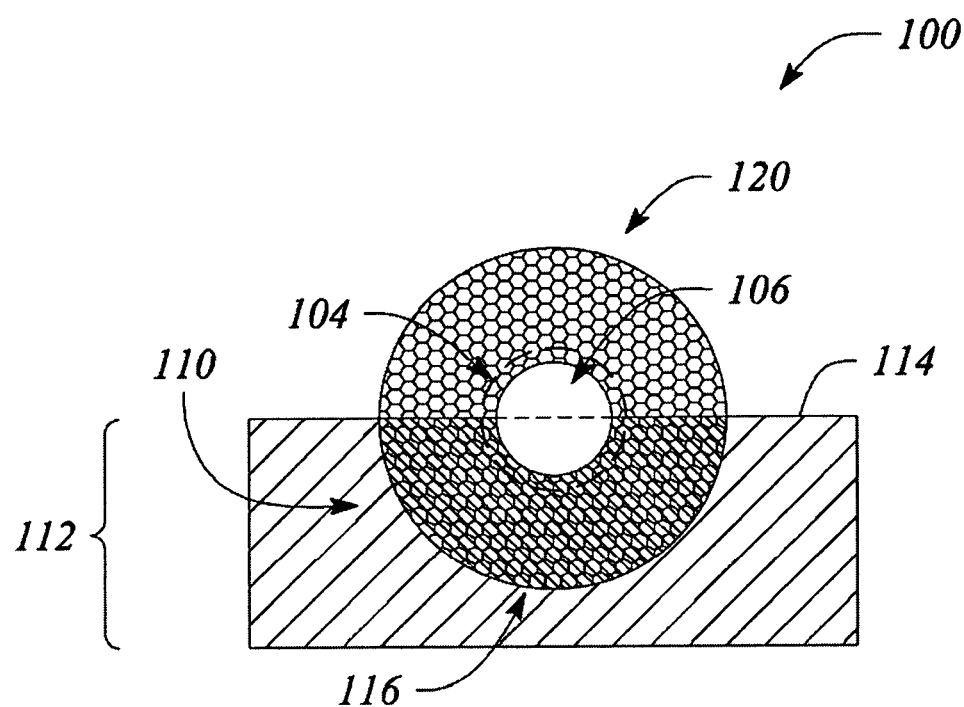
FIG. 3 illustrates a cross sectional view of an optical sensor, according to another embodiment of the present invention.

FIG. 3 illustrates a cross section of an optical sensor 100, according to another embodiment. In particular, as illustrated in FIG. 3, the optical waveguide layer 110 comprises another half-core hollow optical waveguide 116 embedded in a surface 114 of the substrate 112. Optical guiding properties of the other half-core optical waveguide 116 enable it to function as the optical waveguide layer 110 according to embodiments of the present invention. For example, the optical path 104 (the dashed line circle in FIG. 3) essentially contained within the perimeter of combined hollow half-cores of the optical waveguides 120, 116 in this embodiment.

The optical sensor 100 determines a characteristic of the analyte 102 from or by way of optical spectroscopy. Namely, the optical signal interacts with the analyte 102 to produce a spectroscopic product, as has already been discussed. In various embodiments, the optical spectroscopy may employ one or more of optical absorption, fluorescence and Raman scattering.

For example, the characteristic of the analyte 102 may be determined from a spectrum resulting from the analyte 102 differentially absorbing particular frequencies of the optical signal. In another example, one or more of a fluorescent dye, an inherent fluorescence of the analyte 102, and a stimulated fluorescence produced by an interaction between the analyte 102 and a fluorescent material collocated with (e.g., attached to) the analyte 102 may be employed to determine the characteristic. In yet another example, Raman scattering from the analyte 102 illuminated by (he optical signal may be employed to determine the characteristic. The Raman scattering may be enhanced by a Raman active substance collocated with (e.g., in colloidal suspension with or on a surface adjacent to) the analyte 102.

Referring again to FIG. 2A, in some embodiments the optical sensor 100 further comprises a Raman-active surface 130 in the channel 106. The Raman-active surface 130 in the channel 106 in the presence of the optical signal enhances the Raman scattering from the analyte 102 adsorbed thereon. For example, the Raman-active surface 130 may exhibit localized surface plasmons (e.g., a localized surface plasmonic resonance) that enhances the Raman scattering signal produced by the analyte 102. In particular, the Raman-active surface 130 may be a material deposited on one or both of a first wall provided by the substrate surface 114, as illustrated in FIG. 2A, and a second wall provided by the interior surface of the hollow core optical waveguide 120. In such embodiments, a spectroscopic interaction between the analyte 102 and the Raman-active surface 130 may comprises one or both of surface enhanced Raman scattering (SERS) and surface enhanced resonant Raman scattering (SERRS).

In some embodiments, the Raman-active surface 130 comprises nanostructures. Examples of nanostructures include, but are not limited to, nanodots, nanoparticles, and nanowires, as well as more complex nano-scale structures. The nanostructures are deposited on one or both of the interior surface of the hollow core optical waveguide 120 and a portion of the surface 114 of the optical waveguide layer 110 within the channel 106. In some embodiments, the nanostructures comprise one or both of a metal and a metal oxide. For example, nanostructures of silver (Ag), gold (Au) or copper (Cu) having a size in a range from 1 nanometer (nm) to 100 nm may be deposited on the surfaces. Deposition of the nanostructures may employ self-assembly on the surface(s) from a colloidal suspension, for example. Other materials including, but not limited to, a polymer may be employed as the Raman-active surface.

Figure 4:
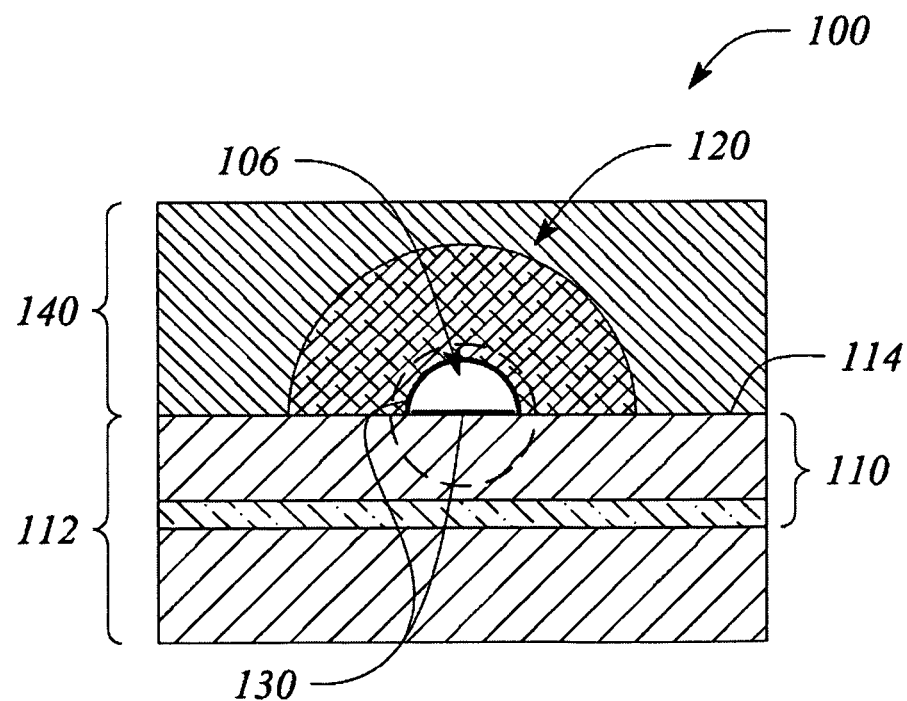
FIG. 4 illustrates a cross sectional view of an optical sensor, according to another embodiment of the present invention.

FIG. 4 illustrates a cross sectional view of an optical sensor 100, according to another embodiment of the present invention. The optical sensor 100 comprises the elements described above for the embodiments of FIGS. 2A and 2B. Moreover, as illustrated in FIG. 4, the optical sensor 100 further comprises a cover layer 140. The half-core hollow optical waveguide 120 is embedded in the cover layer 140 and the cover layer 140 is adjacent to the surface 114 of the substrate 112. In some embodiments, the cover layer 140 is applied or affixed to the surface 114 after the half-core hollow optical waveguide 120 is affixed to the surface 114 of the substrate 112. For example, the cover layer 140 may comprise a material that is deposited over the surface 114 and a previously affixed half-core hollow optical waveguide 120. Alternatively, the cover layer 140 may be fabricated with the half-core hollow optical waveguide 120 embedded therein prior to being affixed to the surface 114. For example, the cover layer 140 may be substrate having grooves into which the half-core hollow optical waveguide 120 is affixed. The cover layer 140 is then applied to the surface 114 and fixed in place by gluing or wafer bonding the cover layer 140 into place, for example. FIG. 4 also illustrates the Raman-active surface 130 applied to interior surfaces of the hollow core half-core hollow optical waveguide 120 as well as to the surface 114 within the channel 106.

Figure 5:
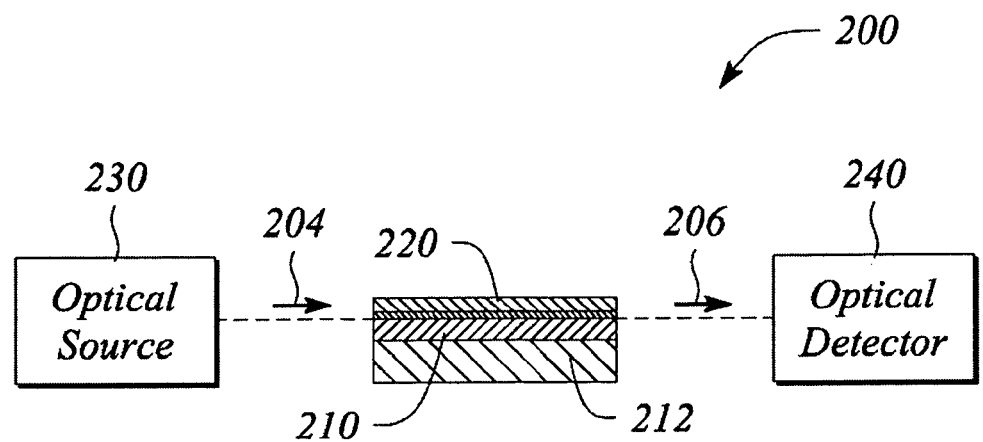
FIG. 5 illustrates a block diagram of an optical sensor system, according to an embodiment of the present invention.

FIG. 5 illustrates a block diagram of an optical sensor system 200, according to an embodiment of the present invention. As illustrated, the optical sensor system 200 determines a characteristic of an analyte or an analyte material from a spectroscopic product of an interaction between an optical signal 204 and the analyte. The spectroscopic product is contained in response signal 206.

The optical sensor system 200 comprises an optical waveguide layer 210. The optical waveguide layer 210 is a part of a substrate 212. In particular, the optical waveguide layer 210 is adjacent to a surface of the substrate 212. In some embodiments, the optical waveguide layer 210 comprises a slab waveguide. In other embodiments, the optical waveguide layer 210 comprises a half-core hollow optical waveguide embedded in the substrate surface. In some embodiments, the optical waveguide layer 210 is essentially similar to the optical waveguide layer 110 described above with respect to the optical sensor 100.

The optical sensor system 200 further comprises a half-core hollow optical waveguide 220. The half-core hollow optical waveguide 220 is adjacent to the substrate surface. Together, the optical waveguide layer 210 and the half-core hollow optical waveguide 220 form an optical path. The half-core hollow optical waveguide 220 provides a hollow core that is collinear with a longitudinal axis of the half-core hollow optical waveguide 220. The hollow core in conjunction with the substrate surface forms a channel that is within an optical field region of the optical signal 204. In some embodiments, the half-core hollow optical waveguide 220 is essentially similar to the half-core hollow optical waveguide 120 described above with respect to the optical sensor 100.

The optical sensor system 200 further comprises an optical source 230. The optical source 230 is located at an input of the optical path formed by the optical waveguide layer 210 and half-core hollow optical waveguide 220. The optical source 230 produces the optical signal 204. For example, the optical source 230 may comprise a laser.

The optical sensor system 200 further comprises an optical detector 240. The optical detector 240 is located at an output of the optical path and receives the response signal 206 containing a spectroscopic product. The spectroscopic product is a result of an interaction between a material to be analyzed (i.e., analyte) within the channel and the optical signal 204 produced by the optical source 230. In some embodiments, the optical detector 240 comprises a photodetector. In other embodiments, the optical detector 240 may comprise a diffraction grating followed by a plurality of photodetectors arranged in an array to facilitate detection and characterization of a spectrum of the response signal 206.

In some embodiments, the optical sensor system 200 is an integrated system. In particular, the elements of the system may all be realized on the substrate (not illustrated). For example, the substrate may comprise a semiconductor material (e.g., Si). The optical source and optical detector may be fabricated as integrated circuit components formed within the semiconductor material using conventional photonic device manufacturing methods.

In some embodiments, the optical sensor system 200 may further comprise components that deliver the analyte to the channel and/or remove the analyte from the channel (not illustrated). For example, a microfluidic channel fabricated in the substrate may be provided that introduces the analyte (e.g., as a fluid) to the channel.

In some embodiments, the optical sensor system 200 further comprises a Raman-active surface (not illustrated in FIG. 5) in the channel and within the optical field region of the optical path. The Raman-active surface may be formed on one or both of a surface of the hollow core and a portion of the substrate surface that coincides with the hollow core (i.e., walls of the channel), for example. The Raman-active surface interacts with the analyte material in the channel during a spectroscopic analysis to yield spectroscopic products by one or both of SERS and SERRS. The Raman-active surface may be essentially similar to the Raman-active surface 130 described above with respect to the optical sensor 100.

In some embodiments, the optical sensor system 200 further comprises a cover layer (not illustrated). The cover layer is located adjacent to the half-core hollow optical waveguide 220 and the substrate surface. In some embodiments, the half-core hollow optical waveguide 220 is embedded in the cover layer. The cover layer supports the embedded half-core hollow optical waveguide 220. The cover layer may further provide an alignment between the half-core hollow optical waveguide 220 and one or more of the substrate having the optical waveguide layer 210 and other half-core hollow-optical waveguides. In some embodiments, the cover layer may be essentially similar to the cover layer 140 described above with respect to the optical sensor 100.

Figure 6:
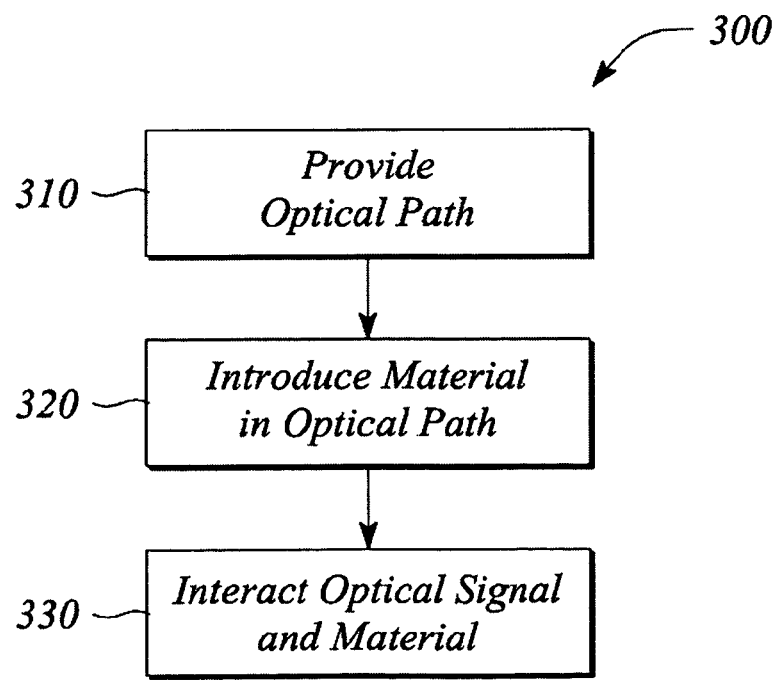
FIG. 6 illustrates a flow chart of a method of optical sensing, according to an embodiment of the present invention.

FIG. 6 illustrates a flow chart of a method 300 of optical sensing, according to an embodiment of the present invention. The method 300 of optical sensing comprises providing 310 an optical path. The provided 310 optical path is formed by a half-core hollow optical waveguide adjacent to an optical waveguide layer of a substrate. The half-core optical waveguide has a hollow core along a longitudinal axis that extends along the optical path. The hollow core cooperatively forms a channel with a surface of the substrate such that the channel also extends along the optical path.

The optical waveguide layer may be essentially similar to the optical waveguide layer 110 described above with respect to the optical sensor 100. Similarly, the half-core hollow optical waveguide may be essentially similar to the half-core hollow optical waveguide 120 described above with respect to the optical sensor 100.

In some embodiments, the method 300 further comprises providing a Raman-active material on a wall of the channel In some embodiments, the Raman-active material is provided on a surface of one or both of the half-core hollow waveguide and the optical waveguide layer that form the channel. In such embodiments, the analyte material interacts with the Raman-active material to produce a spectroscopic response may comprise one or both of surface enhanced Raman scattering (SERS) and surface enhanced resonant Raman scattering (SERRS).

Figure 7A:
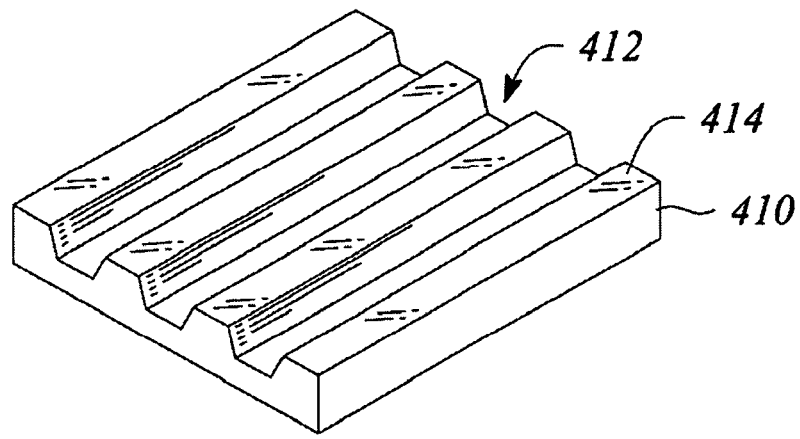
FIGS. 7A-7C illustrate perspective views of a substrate during an exemplary method of bisecting a hollow core optical fiber to produce a half-core hollow optical waveguide, according to an embodiment of the present invention.
Figure 7B:
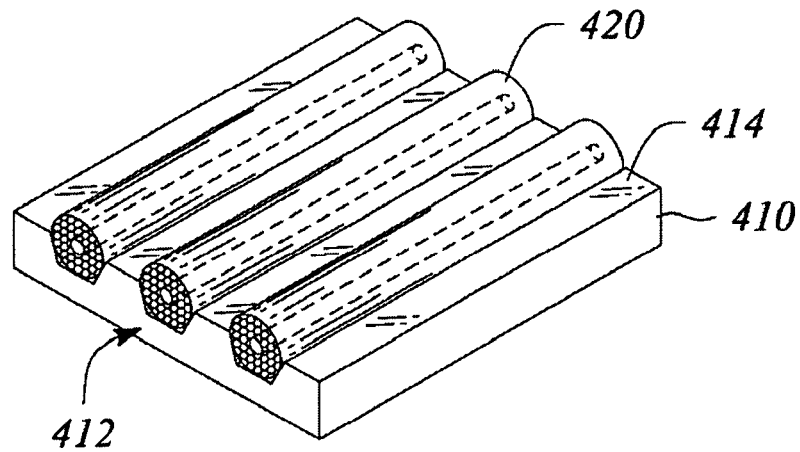
Figure 7C:
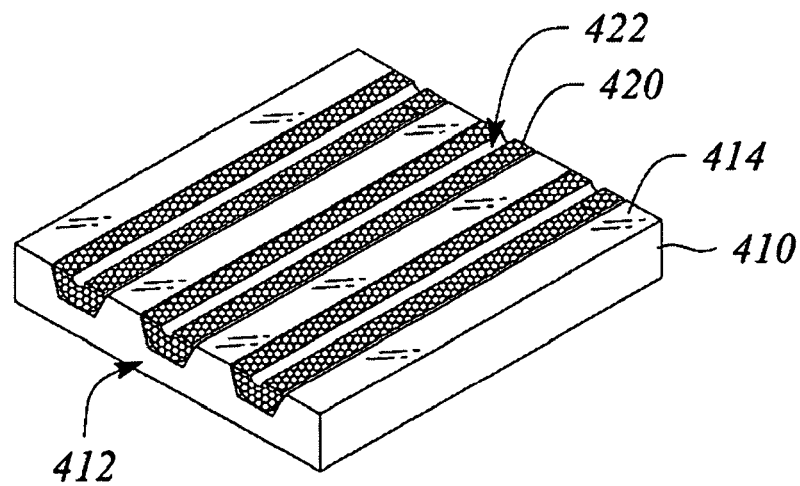

The half-core hollow optical waveguide may be produced by bisecting a hollow core optical fiber, for example. FIGS. 7A-7C illustrate perspective views of a substrate during an exemplar) method of bisecting a hollow core optical fiber to produce a half-core hollow optical waveguide, according to an embodiment of the present invention. As illustrated in FIG. 7A, a substrate 410 is provided The substrate has a groove 412 formed in a surface 414. The groove may be formed by etching or molding, for example.

As illustrated in FIG. 7B, a hollow core optical fiber 420 (e.g., a holey fiber) is embedded in the surface 414 by affixing the hollow core optical fiber in the groove 412. For example, the hollow core optical fiber 420 may be affixed using a bonding agent (e.g., epoxy resin). As illustrated, the groove 412 has a depth that is approximately equal to one half of an overall thickness or diameter of the hollow core optical fiber 420. As such, when affixed in the groove, approximately half of the thickness of the hollow core optical fiber 420 extends above the surface 414 of the substrate 410. In another example (not illustrated), the substrate may be formed around the hollow core optical fiber (e.g., by molding or another related process).

FIG. 7C illustrates a result of removing a portion of the hollow core optical fiber 420 of FIG. 7B that extends above the substrate surface 414. In some embodiments, removing may be accomplished by polishing the substrate surface 414. Polishing may be one or both of mechanical and chemical polishing, for example. In some embodiments (not illustrated), a portion of the substrate surface 414 is removed as well as the portion of the hollow core optical fiber 420. For example, the hollow core optical fiber 420 may be embedded relatively deeply in the substrate surface 414 such that some of the substrate surface 414 must be removed to expose the hollow core 422.

Once the portion is removed, the remaining portion of the hollow core optical waveguide 420 becomes or is the half-core hollow optical waveguide. In particular, removing the portion exposes an inside of the hollow core of the hollow core optical waveguide (i.e. a half-core side of the hollow core optical waveguide is exposed). In some embodiments, the polished substrate 412 with the affixed half-core hollow optical waveguide may be employed directly as the cover or cover layer 140 with the embedded half-core optical waveguide described above with respect to the optical sensor 100. Alternatively, the half-core optical waveguide may be freed from the substrate 412 and employed as a member of the optical path and the channel separate and apart from the substrate 412 used to bisect the hollow core optical fiber.

The method 300 of optical sensing further comprises introducing 320 a material to be analyzed into the channel collocated with the optical path. For example, the analyte material may be a fluid or may be suspended in a fluid. The analyte material may be introduced 320 by allowing or causing the fluid to flow into the channel from an end of the channel, for example. The fluid may be injected into an input port (i.e., input end) by opening a valve or stop cock. The fluid may then flow through the channel due to an injection pressure applied to the fluid. After flowing through the channel the fluid may then exit the channel at an exit port or end, for example.

The method 300 of optical sensing further comprises interacting 330 an optical signal with the analyte material in the channel. In particular, the interaction 330 produces a spectroscopic response. Both the optical signal and the spectroscopic response are guided along the optical path by a combined action of the optical waveguide layer and the half-core hollow optical waveguide. The spectroscopic response is characteristic of the analyte material.

Thus, there have been described embodiments of an optical sensor, an optical sensing system and a method of optical sensing employing a hollow core optical waveguide. It should be understood that the above-described embodiments are merely illustrative of some of the many specific embodiments that represent the principles of the present invention. Clearly, those skilled in the art can readily devise numerous other arrangements without departing from the scope of the present invention as defined by the following claims.

What is claimed is:

1. An optical sensor comprising:
an optical waveguide layer adjacent to a surface of a substrate; and a half-core hollow optical waveguide, a half-core side of the hollow optical waveguide being adjacent to a surface of the optical waveguide layer, the half-core hollow optical waveguide and the optical waveguide layer cooperatively forming both an optical path that confines and guides an optical signal and an internal hollow channel that extend longitudinally along a hollow core of the half-core hollow optical waveguide, wherein a spectroscopic interaction between an analyte within the channel and an optical signal propagating along the optical path determines a characteristic of the analyte.

2. The optical sensor of claim 1, wherein the analyte is a fluid flowing through the channel.

3. The optical sensor of claim 1, wherein the half-core hollow optical waveguide comprises a longitudinal portion of a bisected holey optical waveguide, the hollow core being a longitudinally bisected hole of the holey optical waveguide.

4. The optical sensor of claim 1, wherein the half-core hollow optical waveguide comprises a longitudinal portion of a bisected hollow metal channel waveguide.

5. The optical sensor of claim 1, wherein spectroscopic interaction is one or more of optical absorption, fluorescence, luminescence, and Raman scattering.

6. The optical sensor of claim 1, further comprising a Raman-active surface in the channel and within an optical field region of the optical path, wherein the spectroscopic interaction is one or more of surface enhanced Raman scattering, surface enhanced resonant Raman scattering, and surface enhanced hyper Raman scattering.

7. The optical sensor of claim 6, wherein the Raman-active surface comprises nanostructures deposited on one or both of an interior surface of the hollow core and a portion of a surface of the optical waveguide layer within the channel.

8. The optical sensor of claim 7, wherein the nanostructures comprise one or both of a metal and a metal oxide.

9. The optical sensor of claim 1, further comprising a cover layer adjacent to the optical waveguide layer on the substrate surface, the half-core hollow optical waveguide being embedded in the cover layer.

10. The optical sensor of claim 1, wherein the optical waveguide layer comprises one or more of a slab waveguide, a ridge-loaded optical waveguide and a reverse ridge-loaded optical waveguide.

11. The optical sensor of claim 1, wherein the optical waveguide layer comprises an embedded half-core hollow optical waveguide, a hollow half-core side of both half-core hollow optical waveguides being adjacent at the substrate surface along a longitudinal axis, such that the adjacent half-cores of the two hollow optical waveguides form the hollow channel.

12. The optical sensor of claim 1, further comprising:
an optical source that produces the optical signal; and
a detector that receives a response signal from an output of the optical path, the detector characterizing the spectroscopic interaction to determine the characteristic of the analyte.

13. An optical sensor system comprising:
an optical waveguide layer in a substrate and adjacent to a surface of the substrate;
a half-core hollow optical waveguide having a longitudinal axis and a hollow core collinear with the longitudinal axis, the half-core hollow optical waveguide cooperatively forming both an internal hollow channel and an optical path with the optical waveguide layer, the channel being within an optical field region of the optical path;
an optical source at an input of the optical path; and
an optical detector at an output of the optical path,
wherein the optical detector receives a response signal containing a spectroscopic product of an interaction within the channel between an analyte material to be analyzed and an optical signal produced by the optical source.

14. The optical sensor system of claim 13, wherein the substrate comprises a semiconductor material, the optical source and optical detector being integrated circuit components formed within the semiconductor material.

15. The optical sensor system of claim 13, wherein the substrate further comprises a microfluidic channel that introduces the analyte material into the channel.

16. The optical sensor system of claim 13, further comprising a cover layer adjacent to the surface of the substrate, the half-core hollow optical waveguide being embedded in the cover layer.

17. The optical sensor system of claim 13, further comprising a Raman-active surface in the channel and within the optical field region of the optical path, wherein the spectroscopic product is a result of one or both of surface enhanced Raman scattering (SERS) and surface enhanced resonant Raman scattering (SERRS).

18. A method of optical sensing, the method comprising:
providing an optical path formed by a half-core hollow optical waveguide adjacent to an optical waveguide layer of a substrate, the half-core hollow optical waveguide having a hollow core that cooperatively forms an internal channel with a surface of the substrate such that the channel extends along the optical path;
introducing an analyte into the channel; and
interacting an optical signal with the analyte within the channel to produce a spectroscopic response, the optical signal and the spectroscopic response being guided along the optical path,
wherein the spectroscopic response is characteristic of the analyte.

19. The method of optical sensing of claim 18, further comprising providing a Raman-active material on a surface of the channel, wherein the spectroscopic response is one of surface enhanced Raman scattering (SERS) and surface enhanced resonant Raman scattering.

20. The method of optical sensing of claim 18, wherein providing the optical path comprises:
providing a hollow core optical fiber;
embedding the hollow core optical fiber in a surface of a carrier substrate;
bisecting the hollow core optical fiber to expose the hollow core at the surface; and
bonding the carrier substrate to a surface of the optical waveguide layer, the hollow core being adjacent to the surface of the optical waveguide, such that the optical path is formed coextensive with the internal channel.

21. The optical sensor of claim 1, wherein the optical waveguide layer comprises a different type of optical waveguide than a type of optical waveguide of the half-core hollow optical waveguide.

22. The optical sensor of claim 1, wherein the half-core optical waveguide comprises one of a metal channel optical waveguide, a photonic crystal optical waveguide, a photonic bandgap (PBG) optical fiber, a Bragg fiber and a holey fiber.

23. The optical sensor of claim 1, wherein the optical waveguide layer adjacent to a surface of a substrate comprises a slab waveguide.

* * * * *